(12) United States Patent
Bratkovski

(10) Patent No.: US 7,397,559 B1
(45) Date of Patent: Jul. 8, 2008

(54) SURFACE PLASMON ENHANCED RAMAN SPECTROSCOPY

(75) Inventor: Alexandre Bratkovski, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1 day.

(21) Appl. No.: 11/657,424

(22) Filed: Jan. 23, 2007

(51) Int. Cl.
*G01J 3/44* (2006.01)
*G01N 21/65* (2006.01)

(52) U.S. Cl. ..................................... 356/301
(58) Field of Classification Search .................. 356/301
See application file for complete search history.

(56) References Cited

U.S. PATENT DOCUMENTS

| 5,341,215 | A | 8/1994 | Seher | |
|---|---|---|---|---|
| 7,012,687 | B2 * | 3/2006 | Blumberg et al. | ........... 356/301 |
| 7,057,732 | B2 | 6/2006 | Jorgenson et al. | |

OTHER PUBLICATIONS

Barnes, W., et al., "Surface Plasmon Subwavelength Optics," Nature, vol. 424, pp. 824-830, 2003.
Bouhelier, A. et. al., "Plasmon Optics of structured Silver Films," 2001, American Physical Society, Phys. Rev. B., vol. 63, No. 155404, pp. 1-9.
Brolo, A., et. al., "Enhanced Fluorescence from Arrays of Nanoholes in Gold Film," 2005, Jrnl. American Chem. Soc., vol. 127, No. 42, pp. 14936-14941.
Futamata, M., "Surface Plamon Polariton Enhanced Raman Scattering . . . Dielectric Prop. of Constituents," 1995, Amer. Chem. Soc., Langmuir, vol. 11, pp. 3894-3901.
Futamata, M., "Highly-sensitive ATR Raman Spectroscopy using Surface-Plasmon-Polariton," 2000, Int. J. Vibrational Spectrosc., vol. 4, pp. 9-23.
Hu, W., et. al., "Studying Protein Struct. Changes based on Surface Plasmon Res. and Surface-enhanced Raman Scattering,"2004, Proc. of SPIE, vol. 5327, pp. 88-94.
Kats, W., et al., "Resonance Optical Transmission through . . . Periodically Modul. Metal Films," 2005, Telecomm. and Radio Eng., ISSN 0040-2508, vol. 63, No. 11, pp. 997-1021.
Rodrigues, K., et. al., "Enhanced Infrared Absorp. of Self-Assembled Alkanethiol Monolayers using . . . Subwavelength Apertures," 2004, J. Chem. Phys., vol. 121, No. 18, pp. 8671-8675.
Yih, J., et. al., "A Compact Surface Plasmon Res. and Surface-Enhanc., Raman Scattering Sensing Device," 2004, Proc. of SPIE, vol. 5327, pp. 5-9.
Serulla, D., et. al., "Sensing Molecular Prop. by ATR-SPP Raman Spect. on Electrochem. Struc. Sensor Chips," 2003, Elsevier Ltd., Electrochimica Acta, vol. 48, pp. 2943-2947.

* cited by examiner

*Primary Examiner*—F. L Evans

(57) ABSTRACT

An apparatus and related methods for spectroscopic analysis of analyte molecules is described. The analyte molecules are disposed near a metallic film that is positioned between a first medium on a first side and a second medium on a second side, the second medium being of higher refractive index than the first medium. A radiation source provides excitation radiation that propagates through the second medium toward the metallic film. The second medium and the metallic film are positioned in evanescent communication with respect to the excitation radiation, and the metallic film comprises lithographically patterned features designed to intensify surface plasmon resonance along the metallic film to promote the emission of Raman radiation from the analyte molecules. A radiation detector detects the Raman radiation emitted from the analyte molecules.

20 Claims, 3 Drawing Sheets

US 7,397,559 B1

SURFACE PLASMON ENHANCED RAMAN SPECTROSCOPY

FIELD

This patent specification relates to Raman spectroscopy. More particularly, this patent specification relates to facilitating enhanced Raman signal emission from analyte molecules for spectroscopic analysis thereof.

BACKGROUND

Raman spectroscopy is a technique for performing chemical analysis. High intensity monochromatic light, such as that provided by a laser, is directed onto an analyte molecule (or sample) that is to be chemically analyzed. A majority of the incident photons are elastically scattered by the analyte molecule, the elastically scattered photons having the same energy (and, therefore, the same frequency) as the incident photons. This elastic scattering is termed Rayleigh scattering, and the elastically scattered photons and radiation are termed Rayleigh photons and Rayleigh radiation, respectively. However, a small fraction of the photons (e.g., about 1 in $10^7$ photons) are inelastically scattered by the analyte molecules. These inelastically scattered photons have a different frequency than the incident photons. This inelastic scattering of photons is termed the Raman effect. The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the Stokes radiation. A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the anti-Stokes radiation.

The Stokes and the anti-Stokes radiation is detected by a detector, such as a photomultiplier or a wavelength-dispersive spectrometer, which converts the energy of the impinging photons into an electrical signal. The characteristics of the electrical signal are at least partially a function of the energy (or wavelength, frequency, wave number, etc.) of the impinging photons and the number of the impinging photons per unit time (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency or, equivalently and more commonly, their wavenumber in units of inverse centimeters. A Raman spectrum readout is often presented as a plot of intensity versus Raman shift, the Raman shift being defined as a difference between the wavenumbers of the source radiation (excitation radiation) and the Raman-scattered radiation. Peaks and valleys that are meaningful for purposes of chemical analysis are typically for Raman shifts in the range of 500 $cm^{-1}$-2000 $cm^{-1}$, which for a typical source wavelength of 1000 nm would correspond to Raman-scattered photons having wavelengths between 1050 nm-1250 nm.

This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Unfortunately, molecular Raman scattering is a weak "two photon" process of lower probability than "single photon" processes such as IR absorption, and is thus a more difficult process to measure. Powerful, costly laser sources typically are required to generate high intensity excitation radiation to increase the weak Raman signal for detection. Surface enhanced Raman spectroscopy (SERS) is a technique that allows for generation of a stronger Raman signal from an analyte relative to non-SERS Raman spectroscopy for a sample with the same number of analyte molecules. In SERS, the analyte molecules are adsorbed onto, or placed adjacent to, an activated metal surface or structure, termed herein a SERS-active structure. The interactions between the molecules and the surface cause an increase in the strength of the Raman signal. Several SERS-active structures have been employed in SERS techniques, including activated electrodes in electrolytic cells, activated metal colloid solutions, and activated metal substrates such as a roughened metal surface or metal islands formed on a substrate.

Hyper Raman spectroscopy refers to the analysis of Raman signals near a second (or higher) harmonic of the monochromatic excitation beam. Hyper Raman signals, also termed harmonic Raman signals, result from non-linear effects in which the vibrational modes of the analyte molecule(s) interact with the second (or higher) harmonic of the excitation beam. Hyper Raman spectroscopy can provide valuable additional insight into the characteristics of the analyte molecules, but requires very high power to achieve appreciable spectral readings. SERS-type Raman signal enhancement approaches can often be used to boost the hyper Raman spectrum as well.

Issues arise and/or remain with respect to one or more of the above-described Raman signal enhancement methods that are at least partially resolved by one or more of the embodiments described herein. For example, the Raman signal intensification produced by a SERS-active material can be highly sensitive to small variations in the localized positions of structures, bumps, or cavities therein. Substantial portions of a particular SERS-active surface can be non-enhancing, while only a small number of unpredictably located "hot spots" on that surface are effectively enhancing. It would be desirable to provide for Raman signal intensification having one or more of increased Raman signal enhancement, increased spatial uniformity of response across the sample, and increased range of analytes that can be spectroscopically analyzed. As another example, it would be desirable to provide for increased intensification of second (or higher) harmonic Raman signals. Other issues arise as would be apparent to one skilled in the art upon reading the present disclosure.

SUMMARY

In one embodiment, an apparatus for spectroscopic analysis of a plurality of analyte molecules is provided, comprising a metallic film near which a plurality of analyte molecules is disposed, a first medium on a first side of the metallic film, and a second medium on a second side of the metallic film. The second medium is of higher refractive index than the first medium. The apparatus further comprises a radiation source providing excitation radiation that propagates through the second medium toward the metallic film. The second medium and the metallic film are positioned in evanescent communication with respect to the excitation radiation. The apparatus further comprises a radiation detector detecting Raman radiation emitted from the analyte molecules. The metallic film comprises lithographically patterned features designed to intensify surface plasmon resonance along the metallic film to promote the emission of the Raman radiation from the analyte molecules.

Also provided is a method for Raman spectroscopy, comprising providing a metallic film near which a plurality of analyte molecules is disposed, the metallic film being positioned between a first medium on a first side and a second medium on a second side, the second medium being of higher refractive index than the first medium, the second medium being positioned in evanescent communication with the metallic film with respect to radiation of at least one predetermined frequency. The method further comprises providing excitation radiation at the at least one predetermined frequency that propagates through the second medium toward the metallic film. The method further comprises detecting Raman radiation emitted from the analyte molecules. The metallic film comprises lithographically patterned features designed to intensify surface plasmon resonance along the metallic film to promote the emission of the Raman radiation from the analyte molecules.

Also provided is an apparatus for Raman spectroscopy of a plurality of analyte molecules, comprising a metallic film having an upper surface near which the analyte molecules are disposed, means for providing excitation radiation propagating toward a lower surface of the metallic film from therebeneath, prismatic means for coupling the incident excitation radiation into surface plasmons on the metallic film, and means for detecting Raman radiation emitted in a generally upward direction from the analyte molecules. The metallic film comprises lithographically patterned features designed to intensify the surface plasmons to promote the emission of the Raman radiation from the analyte molecules.

DETAILED DESCRIPTION

Figure 1:
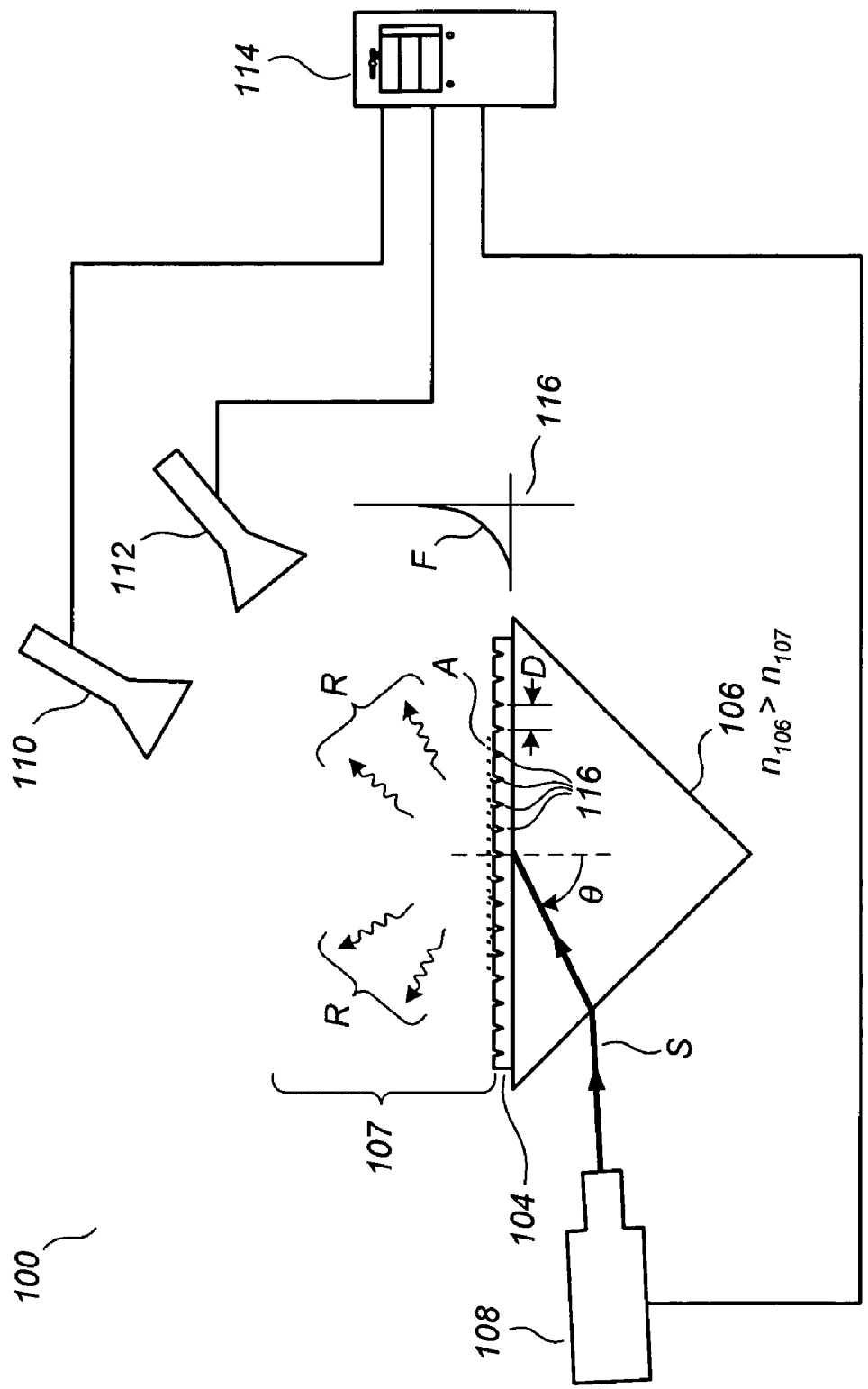
FIG. 1 illustrates a Raman spectroscopy apparatus according to an embodiment.

FIG. 1 illustrates a Raman spectroscopy apparatus 100 according to an embodiment, comprising a metallic film 104, a prism 106, an excitation radiation source 108, and Raman radiation detectors 110 and 112. A processor 114 is also provided for controlling and/or receiving information from the radiation source 108, the Raman radiation detectors 110 and 112, and other related equipment as necessary. In the space immediately above the metallic film 104 is a first medium 107 having an index of refraction $n_{107}$ less than an index of refraction $n_{106}$ of the prism 106. The first medium 107 can comprise, for example, air (or other gas) or a liquid of sufficiently lower refractive index than $n_{106}$.

A plurality of analyte molecules "A" is disposed near an upper surface of the metallic film 104. By way of example and not by way of limitation, the metallic film 104 may comprise gold and have a thickness of 20-40 nm. Other suitable metals may include silver, copper, platinum, palladium, titanium, chromium, and aluminum. The metallic film 104 is preferably derivatized or functionalized by attachment of receptors or ligands (not shown) that promote the binding of a particular analyte molecule in close proximity to its upper surface. The ligand may be repulsive or neutral relative to other molecules. The ligand and the analyte molecule may consist of what is often referred to as a specific pair or a recognition pair of molecules. The particular analyte molecule may include, but is not limited to, biomolecules such as nucleic acids, proteins, hormones, sugars, and metabolites. The ligand may include, but is not limited to, antibodies, receptors, and nucleic acids. Techniques for functionalizing surfaces for attachment of particular analyte molecules thereto have been researched and developed extensively in the art of biosensors and bioassays and can be employed.

Figure 2:
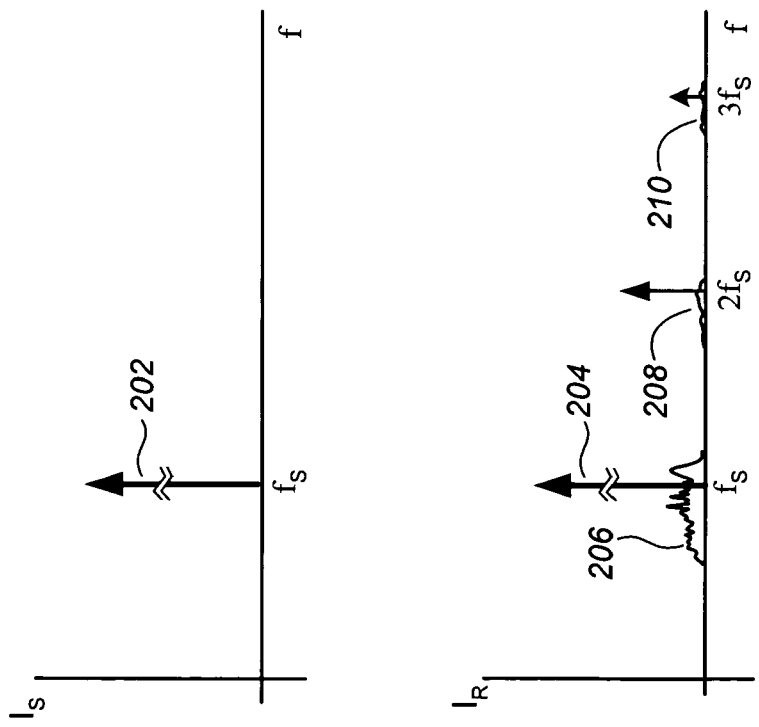
FIG. 2 illustrates spectral plots associated with the Raman spectroscopy apparatus of FIG. 1.

FIG. 2 illustrates spectral plots associated with the Raman spectroscopy apparatus of FIG. 1. The excitation radiation source 108 provides a strong monochromatic excitation radiation beam "S," a spectrum 202 thereof being illustrated in FIG. 2 as a plot of intensity versus frequency. An exemplary range of wavelengths that may be emitted by the excitation radiation source 108 includes wavelengths between about 350 nm and about 2000 nm, although the scope of the present teachings is not so limited.

Referring again to FIG. 1, the prism 106 is positioned in evanescent communication with the metallic film 104 with respect to the incident excitation radiation beam S. As used herein, evanescent communication refers to a configuration in which an evanescent field associated with electromagnetic radiation propagating in a first medium extends beyond a boundary of the first medium into a second medium such that an associated transfer of electromagnetic energy from the first medium to the second medium is achieved. Typically, it is necessary for the first and second media to be separated by substantially less than one wavelength for evanescent communication to be achievable. The evanescent communication between the prism 106 and the metal film 104 is conceptually illustrated in FIG. 1 by a plot 116 of an evanescent field "F" extending outward from an upper boundary of the prism 106 and into the metal film 104.

Figure 7:
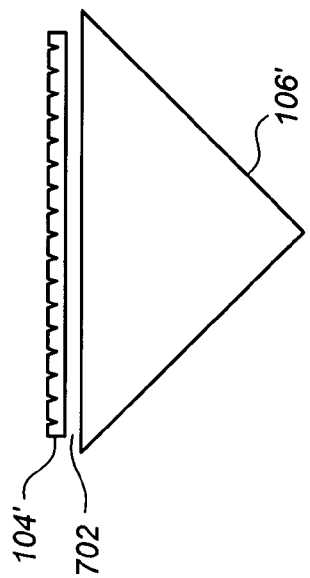
FIG. 7 illustrates an Otto configuration for a prism and a metallic film of the Raman spectroscopy apparatus of FIG. 1 according to an embodiment.

According to the particular embodiment of FIG. 1, the prism 106 and metallic film 104 are disposed in a Kretschmann configuration for achieving evanescent communication at the excitation radiation frequency. In another embodiment, an Otto configuration may be used, as illustrated in FIG. 7, which shows a prism 106' separated from a metallic film 104' by a gap 702. The gap 702 is usually very small (e.g., on the order of 10-20 nm). Kretschmann and Otto configurations are known in the art as being effective methods for coupling incident radiation into surface plasmons of metallic films. However, the scope of the present teachings is not so limited, and other methods for achieving evanescent communication between a metal film and a second medium disposed therebeneath, the second medium having a refractive index greater than that of a first medium disposed above the metallic film, are within the scope of the present teachings.

Figure 3:
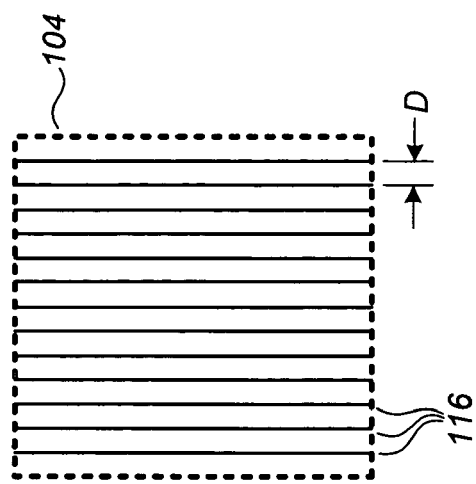
FIGS. 3-6 illustrate top views of metal films suitable for the Raman spectroscopy apparatus of FIG. 1 according to one or more embodiments.
Figure 4:
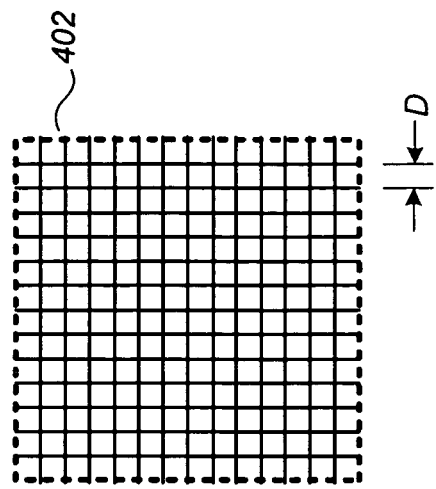

According to an embodiment, the metallic film comprises lithographically patterned features 116 designed to intensify surface plasmon resonance along the metallic film. For the embodiment of FIG. 1, the features 116 comprise periodic grating structures of period D along a single dimension, with a top view of a portion of the metallic film 104 being shown in FIG. 3. Preferably, the period D is greater than or equal to a wavelength of electromagnetic radiation at the excitation beam frequency in the first medium 107 (i.e., the free-space wavelength of the excitation beam divided by $n_{107}$). In another embodiment, the lithographically patterned surface features comprise two-dimensional gratings, as illustrated by a metallic film portion 402 of FIG. 4. In another embodiment, the lithographically patterned surface features comprise a two-dimensional pattern of through holes as illustrated by a metallic film portion 502 of FIG. 5. Although illustrated as being circular in the embodiment of FIG. 5, the through holes may be any of a variety of different geometric shapes without departing from the scope of the present teachings.

Referring again to FIG. 1, and noting that the metallic film 104 does not contain any through holes in the embodiment of FIG. 1, the intensification of surface plasmons provided by the lithographically patterned features 116 according to an embodiment is sufficiently great to cause substantial amounts of radiation "R" to be emitted from the upper surface of the metallic film, the radiation "R" including so-called extraordinary radiation in which surface plasmon energy is coupled back out (out-coupled) into propagating radiation, the radiation "R" further including Rayleigh and Raman components due to the presence of the analyte molecules. For clarity of description, and in view of the fact that the true physics of their generation may not be completely understood (e.g., photon scattering by absorption and re-emission, direct photon emission from interactions with locally strong fields and/ or intense surface plasmons, quantum-mechanical effects), the Raman and Rayleigh components of the radiation "R" are simply referenced herein as being "emitted" from the analyte molecules.

Shown in FIG. 2 is a spectral plot of the radiation "R" including an extraordinary/Rayleigh component 204 and a Raman component 206. Moreover, when the induced surface plasmons are sufficiently intense, the radiation "R" also includes hyper Raman radiation near harmonics of the excitation frequency, as illustrated by the hyper Raman components 208 (second harmonic) and 210 (third harmonic). The use of lithographically patterned surface features provides for more precise control of the shape of the metallic film in the close vicinity of the surface plasmons, leading to an ability to better and more reliability optimize their intensification as compared, for example, to the use of roughened metal surfaces or surfaces with colloidal metallic nanoparticles suspended thereon or therenear.

The distinct Raman radiation detectors 110 and 112 are illustrated in FIG. 1 to represent separate detection of the baseband (i.e., regular or first harmonic) Raman radiation (e.g., by the Raman radiation detector 110) and the hyper Raman or harmonic Raman radiation (e.g., by the Raman radiation detector 112). Typically, the Raman and hyper Raman components of the radiation "R" are emitted isotropically from the analyte molecules. Thus, the particular positioning of Raman radiation detectors 110 and 112 in FIG. 1 is for illustrative purposes only, it being understood that practical collection and measurement of the Raman signals will be achieved by more complex optical components as could be implemented by a person skilled in the art in view of the present disclosure.

Figure 5:
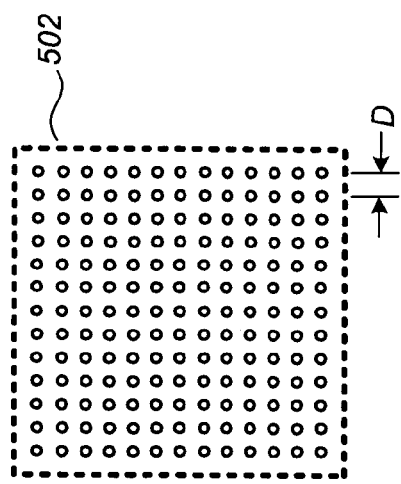

According to another embodiment in which the metallic film 502 of FIG. 5 is used in place of the metallic film 104 in FIG. 1, the radiation "R" may further include "ordinary" radiation, i.e., excitation radiation that propagates directly through the through holes to the upper side of the metallic film 502. However, this component will usually be relatively small because the incident angle θ for best excitation of surface plasmons in the metallic film will generally be greater than the critical angle for the upper interface of the prism 106.

Figure 6:
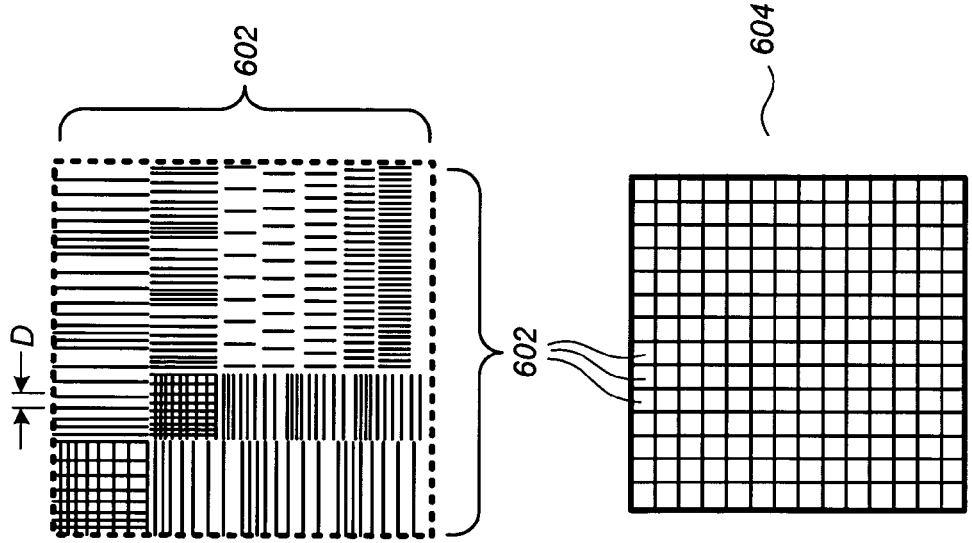

FIG. 6 illustrates a metallic film 604 that may be used in place of the metallic film 104 in FIG. 1, comprising a plurality of sub-arrays 602 having chirped gratings. For this embodiment, the chirping of the gratings at spacings generally in the neighborhood of D can provide an increased range of operation in terms of the range of analyte molecules and/or the range of frequencies across which surface plasmon resonance can be intensified to promote Raman signal emission from the upper surface of the metallic film. The lithographic patterning of the features on the metallic films illustrated in FIG. 1 and FIGS. 3-6 may be formed using known photolithography methods, nanoimprint lithography methods, or other methods.

As stated above, Kretschmann and Otto configurations are known in the art as being effective methods for coupling incident radiation into surface plasmons of metallic films. The Kretschmann and Otto configurations are often used in so-called SPR (Surface Plasmon Resonance) spectroscopy discussed, for example, in the commonly assigned U.S. Pat. No. 5,341,215, which is incorporated by reference herein. It is to be appreciated, however, that although an advantageous, high-percentage coupling of excitation radiation into surface plasmons is achieved by the Raman spectroscopy apparatus of FIG. 1 in a manner similar to the coupling achieved by Kretschmann/Otto SPR spectroscopy methods, the Raman spectroscopy apparatus of FIG. 1 is otherwise significantly different than the SPR spectroscopy teachings of U.S. Pat. No. 5,341,215.

More particularly, a surface plasmon, often interchangeably termed a surface plasmon-polariton (SPP), is a coupled, localized transverse magnetic electromagnetic field/charge density oscillation which may propagate along an interface between two media with dielectric constants of opposite sign, such as a metal and a dielectric. The fields associated with the surface plasmons extend into the media adjacent to the interface. Consequently, the surface plasmons are sensitive to changes in the environment near that metal-dielectric interface. The SPR spectroscopy methods discussed in U.S. Pat. No. 5,341,215 are directed the sensing of certain analytes by virtue of detecting changes to those surface plasmon resonance conditions. The measurements taken in SPR spectroscopy are generally of the amount of p-polarized excitation radiation that is reflected from the upper surface of the prism as the incident angle θ is increased, with a minimum being reached as surface plasmon resonance in the metal film—as perturbed by the nearby analyte molecules—reaches a peak amount at an incident angle $θ_{SPR}$, which may vary according to the nature of the molecules present. In contrast, the embodiment of FIG. 1 uses intensified surface plasmons created by a Kretschmann configuration as an energizing means for causing Raman radiation to be emitted from the analyte molecules, the intensification of surface plasmons being furthered by the presence of lithographically patterned surface features on the metal film, and then measures the emitted Raman radiation.

The particular incidence angle $θ_{MAX}$ of the excitation radiation S for maximum surface plasmon resonance will depend on the specific characteristics of the metal film, the lithographically patterned features, the film thickness, the refractive indices of dielectrics on either side of the metal film, and the type and concentration of analyte molecules "A." However, the incidence angle $\theta_{MAX}$ should of course be greater than both the Brewster angle and the critical angle at the upper surface of the prism 106, just as the peak incident angle $\theta_{SPR}$ for surface plasmon resonance in SPR spectroscopy contexts is greater than both the Brewster angle and the critical angle.

Whereas many alterations and modifications of the embodiments will no doubt become apparent to a person of ordinary skill in the art after having read the foregoing description, it is to be understood that the particular embodiments shown and described by way of illustration are in no way intended to be considered limiting. By way of example, although the analyte molecules in one or more of the embodiments supra are disposed above the metallic film (i.e., opposite the side of the prism and the excitation radiation beam) and the Raman radiation is emitted in a generally upward direction (i.e., away from the metallic film opposite the side of the prism and the excitation radiation beam), in other embodiments the analyte molecules may be positioned between the prism and the metallic film on the lower side of the metallic film, in which case the Raman radiation is emitted in a generally downward direction (i.e., on the same side as the prism and the excitation radiation beam). By way of still further example, multiple similar or different lithographically patterned metallic films can be arrayed together and used with a common analyte sample to achieve any of a variety of goals including, but not limited to, portability, dependability, reusability, cost efficiency, calibration reliability, and/or adaptability for differing analyte molecule types, without departing from the scope of the present teachings. By way of still further example, although lithographically formed features having periods of at least a wavelength in the medium immediately above the metallic film have been found particularly effective, it is not outside the scope of the present teachings to pattern the metallic film with sub-wavelength features, e.g., using nanoimprint lithography, if particular patterns of such features can be found that are effective in intensifying the surface plasmon resonance in the metallic film. Thus, reference to the details of the described embodiments are not intended to limit their scope.

What is claimed is:

1. An apparatus for spectroscopic analysis of a plurality of analyte molecules, comprising:
    a metallic film near which a plurality of analyte molecules is disposed;
    a first medium on a first side of said metallic film;
    a second medium on a second side of said metallic film, the second medium being of higher refractive index than the first medium;
    a radiation source providing excitation radiation that propagates through said second medium toward said metallic film, said second medium and said metallic film being positioned in evanescent communication with respect to said excitation radiation; and
    a radiation detector detecting Raman radiation emitted from said analyte molecules;
    wherein said metallic film comprises lithographically patterned features designed to intensify surface plasmon resonance along said metallic film to promote said emission of said Raman radiation from said analyte molecules.

2. The apparatus of claim 1, wherein said analyte molecules are disposed in said first medium on said first side of said metallic film, and wherein said Raman radiation is emitted into said first medium in a direction away from said metallic film for detection by said radiation detector.

3. The apparatus of claim 2, said metallic film having no through holes at locations near said analyte molecules, said emitted Raman radiation arising from interactions between said analyte molecules and excitation radiation extraordinarily transmitted through said metallic film as facilitated by said intensified surface plasmons.

4. The apparatus of claim 2, said metallic film having a population of through holes at locations near said analyte molecules, said emitted Raman radiation arising from interactions between said analyte molecules and a combination of (a) excitation radiation ordinarily propagated through said through holes and (b) excitation radiation extraordinarily transmitted through said metallic film as facilitated by said intensified surface plasmons.

5. The apparatus of claim 2, wherein said lithographically patterned features comprise periodic gratings having a period not less than a wavelength of said excitation radiation in said first medium.

6. The apparatus of claim 2, wherein said lithographically patterned features comprise a two-dimensional periodic pattern of through holes extending through a thickness of the metallic film and having a period in at least one dimension that is not less than a wavelength of said excitation radiation in said first medium.

7. The apparatus of claim 1, wherein said lithographically patterned features are spatially chirped with respect to at least one of shape, dimension, and spacing.

8. The apparatus of claim 1, wherein said second medium comprises a prism configured in one of a Kretschmann configuration and an Otto configuration with respect to said metallic film.

9. The apparatus of claim 1, wherein said radiation detector comprises:
    a first detector configured to detect Raman radiation near a frequency of said excitation radiation; and
    a second detector configured to detect Raman radiation near a harmonic of said frequency.

10. A method for Raman spectroscopy, comprising:
    providing a metallic film near which a plurality of analyte molecules is disposed, the metallic film being positioned between a first medium on a first side and a second medium on a second side, the second medium being of higher refractive index than the first medium, the second medium being positioned in evanescent communication with said metallic film with respect to radiation of at least one predetermined frequency;
    providing excitation radiation at said at least one predetermined frequency that propagates through said second medium toward said metallic film; and
    detecting Raman radiation emitted from said analyte molecules;
    wherein said metallic film comprises lithographically patterned features designed to intensify surface plasmon resonance along said metallic film to promote said emission of said Raman radiation from said analyte molecules.

11. The method of claim 10, said second medium comprising a prism, wherein said prism is configured in one of a Kretschmann configuration and an Otto configuration with respect to said metallic film.

12. The method of claim 10, wherein said lithographically patterned features comprise at least one of (a) periodic gratings having a period not less than a wavelength of said excitation radiation in said first medium and (b) a two-dimensional periodic pattern of through holes extending through a thickness of the metallic film and having a period in at least one dimension that is not less than said wavelength of said excitation radiation in said first medium.

13. The method of claim 10, wherein said lithographically patterned features are spatially chirped with respect to at least one of shape, dimension, and spacing.

14. The method of claim 10, wherein said detecting comprises detecting Raman radiation near at least one harmonic of said at least one predetermined frequency.

15. The method of claim 10, wherein said analyte molecules are disposed in said first medium on said first side of said metallic film, and wherein said detecting comprises detecting Raman radiation that is emitted into said first medium in a direction away from said metallic film.

16. The method of claim 15, said metallic film having no through holes at locations near said analyte molecules, said emitted Raman radiation arising from interactions between said analyte molecules and excitation radiation extraordinarily transmitted through said metallic film as facilitated by said intensified surface plasmons.

17. The method of claim 15, said metallic film having a population of through holes at locations near said analyte molecules, said emitted Raman radiation arising from interactions between said analyte molecules and a combination of (a) excitation radiation ordinarily propagated through said through holes and (b) excitation radiation extraordinarily transmitted through said metallic film as facilitated by said intensified surface plasmons.

18. An apparatus for Raman spectroscopy of a plurality of analyte molecules, comprising:

a metallic film having an upper surface near which the analyte molecules are disposed;

means for providing excitation radiation propagating toward a lower surface of the metallic film from thereneath;

prismatic means for coupling said incident excitation radiation into surface plasmons on said metallic film; and means for detecting Raman radiation emitted in a generally upward direction from said analyte molecules;

wherein said metallic film comprises lithographically patterned features designed to intensify said surface plasmons to promote said emission of said Raman radiation from said analyte molecules.

19. The apparatus of claim 18, wherein said prismatic means for coupling comprises a prism configured in one of a Kretschmann configuration and an Otto configuration with respect to said metallic film, wherein said metallic film has no through holes at locations near said analyte molecules, and wherein said emitted Raman radiation arises from interactions between said analyte molecules and excitation radiation extraordinarily transmitted through said metallic film as facilitated by said intensified surface plasmons.

20. The apparatus of claim 19, wherein said lithographically patterned features comprise at least one of (a) periodic gratings having a period not less than a wavelength of said excitation radiation and (b) a two-dimensional periodic pattern of through holes extending through a thickness of the metallic film and having a period in at least one dimension that is not less than said wavelength.

* * * * *